(12) United States Patent
Kwon et al.

(10) Patent No.: US 9,949,960 B2
(45) Date of Patent: Apr. 24, 2018

(54) PHARMACEUTICAL COMPOSITION FOR PREVENTING OR TREATING MUSCLE WEAKNESS-RELATED DISEASES, CONTAINING BUTYLPYRIDINIUM OR DERIVATIVE THEREOF

(71) Applicants: KOREA RESEARCH INSTITUTE OF BIOSCIENCE AND BIOTECHNOLOGY, Daejeon (KR); SNU R&DB FOUNDATION, Seoul (KR)

(72) Inventors: Ki-Sun Kwon, Daejeon (KR); Sung Sup Park, Daejeon (KR); Sun Gun Chung, Seoul (KR); Kwang-Pyo Lee, Daejeon (KR); Jeong Yi Choi, Daejeon (KR)

(73) Assignees: KOREA RESEARCH INSTITUTE OF BIOSCIENCE AND BIOTECHNOLOGY, Daejeon (KR); SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 15/374,225

(22) Filed: Dec. 9, 2016

(65) Prior Publication Data
US 2017/0112817 A1   Apr. 27, 2017

Related U.S. Application Data (63) Continuation-in-part of application No. PCT/KR2014/006416, filed on Jul. 16, 2014.

(30) Foreign Application Priority Data

Jun. 12, 2014 (KR) .................... 10-2014-0071676

(51) Int. Cl.
*A61K 31/4425*   (2006.01)
(52) U.S. Cl.
CPC .............. *A61K 31/4425* (2013.01)

(58) Field of Classification Search
CPC ................................ A61K 31/4425
See application file for complete search history.

(56) References Cited

FOREIGN PATENT DOCUMENTS

| JP | 2006-517565 A | 7/2006 |
|---|---|---|
| KR | 10-2013-0117017 A | 10/2013 |
| KR | 10-2014-0042759 A | 4/2014 |
| WO | WO 2009/020601 A2 | 2/2009 |
| WO | WO 2013/177176 A1 | 11/2013 |

OTHER PUBLICATIONS

Notification of Reasons for Refusal dated Aug. 22, 2017 in connection with related Japanese Patent Application No. JP 2017-518018.
International Search Report in connection with PCT/KR2014/006416.
Shihuan Kuang and Michael A. Rudnicki, "The emerging biology of satellite cells and their therapeutic potential", Cell Press, .2008, 14, 82-31.
D. D. Thompson, "Aging and sarcopenia", J. Muscoskelet Neuronal Interact, 2007, 7, 344-345.
Nelson Osses, et al., "Inhibition of extracellular matrix assembly induces the expression of osteogenic markers in skeletal muscle cells by a BMP-2 independent mechanism", BMC Cell Biology, Oct. 5, 2009, 10:73.

*Primary Examiner* — Jeffrey S Lundgren
*Assistant Examiner* — Meghan Finn
(74) *Attorney, Agent, or Firm* — John P. White; Cooper & Dunham LLP

(57) ABSTRACT

The present invention relates to A method for promoting the differentiation of myoblasts comprising treating myoblasts with butylpyridinium, a derivative thereof, or a pharmaceutically acceptable salt thereof; a method for strengthening muscles comprising administering butylpyridinium, a derivative thereof, or a pharmaceutically acceptable salt thereof to a subject in need thereof; a feed or feed additive for strengthening muscles comprising butylpyridinium, a derivative thereof, or a pharmaceutically acceptable salt thereof; a method for treating a disease associated with muscle weakness comprising administering butylpyridinium, a derivative thereof, or a pharmaceutically acceptable salt thereof to a subject in need thereof.

4 Claims, 9 Drawing Sheets

A. Grip strength test

[FIG. 5]
B. Rota-rod test

[FIG. 6]
C. Treadmill test

[FIG. 7]

A. Grip strength test

[FIG. 8]

B. Rota-rod test

[FIG. 9]

C. Treadmill test

[FIG. 10]

A. Rota-rod test

B. Treadmill test

A. Immunohistochemistry staining

B. Cross sectional area (CSA) in young mice TA muscle

B. Cross sectional area (CSA) in aged mice TA muscle

[FIG. 15]

PHARMACEUTICAL COMPOSITION FOR PREVENTING OR TREATING MUSCLE WEAKNESS-RELATED DISEASES, CONTAINING BUTYLPYRIDINIUM OR DERIVATIVE THEREOF

CROSS-REFERENCE TO RELATED APPLICATIONS

This application is a continuation-in-part of PCT International Application No. PCT/KR2014/006416, filed Jul. 16, 2014, claiming priority of Korean Patent Application No. KR 10-2014-0071676, filed Jun. 12, 2014, the content of each of which is hereby incorporated by reference into the application.

TECHNICAL FIELD

The present invention relates to a composition for promoting the differentiation of myoblasts comprising butylpyridinium, a derivative thereof, or a pharmaceutically acceptable salt thereof; a pharmaceutical composition for preventing or treating a disease associated with muscle weakness; a food composition for preventing or ameliorating a disease associated with muscle weakness; a composition for strengthening muscles; and a feed or feed additive for strengthening muscles.

Further, the present invention relates to a method for promoting the differentiation of myoblasts using butylpyridinium, a derivative thereof, or a pharmaceutically acceptable salt thereof; a method for preparing differentiated myoblasts; and a method for treating a disease associated with muscle weakness.

BACKGROUND ART

Diseases that cause weakness in muscles include sarcopenia, which progresses with aging; muscular atrophy, which is caused by an imbalance in protein metabolism and a decrease in muscle use; and acardiotrophy, which progresses with starvation, debilitating diseases (cancer, etc.), and aging.

Sarcopenia refers to a reduction in muscle strength due to a decrease in skeletal muscle mass while aging is in progress. The decrease in skeletal muscle mass, which is the most important characteristic of sarcopenia, and additionally the changes in the types of muscle fibers are observed together. Whereas the diameters of Type 1 and Type 2 muscle fibers decrease at a similar rate as aging progresses, under sarcopenia, the diameter of the Type 2 muscle fiber does not change significantly, but the diameter of the Type 1 muscle fiber noticeably decreases. It has been reported that sarcopenia causes senility and functional disorders that occur among the elderly.

Sarcopenia is caused by various factors, but studies regarding each factor are still in progress. Sarcopenia is induced by a reduction in the growth hormone level or neurological changes, changes in physiological activity, changes in metabolism, an increase in the amount of sex hormones or fat and catabolic cytokines, and a change in the balance of protein synthesis and degradation. The most important cause of the decrease in skeletal muscle mass, which is the most pronounced characteristic of sarcopenia, is known to be the reduction of satellite cell activation. Satellite cells are small mononuclear cells located between a basement membrane and a sarcolemma of muscle fibers. These satellite cells are activated by stimuli such as injury or exercise and are proliferated as myoblasts, and as the differentiation is in progress, they fuse with other cells to form multinucleated muscle fibers. Accordingly, as the satellite cell activation is reduced, the ability to regenerate a damaged muscle or responses to differentiation signals is reduced, thereby resulting in a decrease in the muscle formation.

Muscular atrophy is caused by nutritional deficiency or after a long period of physical inactivity, and it is indicated by protein degradation which occurs due to a disruption in the balance between protein synthesis and degradation.

On the other hand, acardiotrophy is caused by starvation, debilitating diseases (cancer, etc.), and senility, myocardial fibers become thinner, and the nucleus becomes concentrated and exhibits anisocytosis. As a result, the volume of muscle fascicles is decreased, the heart as a whole becomes smaller, the size of subepicardial adipose tissues is clearly decreased, and coronary arteries become curved. A consumable dye (lipofuscin) appears at both ends of the nucleus of myocardial fibers as a brown dye, and along with the reduction of adipose tissues, the entire heart displays a brown color.

The treatment methods for sarcopenia include three methods. The first method is exercise. Exercise improves, in the short term, the ability of the protein synthesis of skeletal muscles, and it has been reported to increase muscle strength and mobility in the elderly. However, exercise is not appropriate as a long-term treatment method. The second method is, as a drug treatment, the administration of testosterone or anabolic steroids, but this induces masculinization in females, and in males, side effects such as prostate symptoms may occur. For the other approved method, dehydroepiandrosterone (DHEA) and growth hormones are available, and a study was reported that it is possible to apply these as a treatment method at a region including selective androgen receptor modulators (SARMs) (D. D. Thompson, *J. Musculoskelet Neuronal Interact* 7, 344-345, 2007). In particular, although diet has been known as a treatment method, malnutrition and modern eating habits are inappropriate for maintaining the proper total body mass, according to a nutritional assessment.

Recently, stem cell therapy, in which satellite cells are isolated and differentiated in vitro so that they are introduced into the body, and the method for directly activating satellite cells in the body to promote myogenesis in order to maintain or strengthen the muscle are being highlighted as possible treatment methods for treating muscle weakness such as sarcopenia (Shihuan Kuang, and Michael A. Rudnicki, *Trends in Molecular Medicine* 14, 82-31, 2008).

Therefore, in order to treat diseases associated with muscle weakness, a method for differentiating myoblasts is demanded as a more fundamental method without side effects, and as a result, the development of a substance capable of promoting the differentiation of myoblasts is highly necessary.

DISCLOSURE

Technical Problem

The present inventors made great efforts to develop a medicine to treat a disease associated with muscle weakness that increases the skeletal muscle mass and effectively restores muscle functions, and as a result, the present invention was completed by confirming that a method for promoting the differentiation of myoblasts comprising treating myoblasts with butylpyridinium, a derivative thereof, or a pharmaceutically acceptable salt thereof can promote the differentiation of myoblasts in order to prevent or treat a disease associated with muscle weakness.

Technical Solution

An object of the present invention is to provide a method for promoting the differentiation of myoblasts comprising treating myoblasts with butylpyridinium, a derivative thereof, or a pharmaceutically acceptable salt thereof.

Another object of the present invention is to provide a method for strengthening muscles comprising administering butylpyridinium, a derivative thereof, or a pharmaceutically acceptable salt thereof to a subject in need thereof.

Another object of the present invention is to provide a feed or feed additive for strengthening muscles comprising butylpyridinium, a derivative thereof, or a pharmaceutically acceptable salt thereof.

Another object of the present invention is to provide a method for treating a disease associated with muscle weakness comprising administering butylpyridinium, a derivative thereof, or a pharmaceutically acceptable salt thereof to a subject in need thereof.

Advantageous Effects

According to the present invention, butylpyridinium, a derivative thereof, or a pharmaceutically acceptable salt thereof promotes the differentiation of myoblasts and is capable of forming myotubes and thereby preventing muscle weakness, and can also effectively improve muscle functions. Accordingly, a pharmaceutical composition comprising butylpyridinium, a derivative thereof, or a pharmaceutically acceptable salt thereof can be effectively used to prevent or treat a disease associated with muscle weakness.

BEST MODE

As one aspect of achieving the above objects, one exemplary embodiment of the present invention relates to a composition for promoting the differentiation of myoblasts comprising butylpyridinium, a derivative thereof, or a pharmaceutically acceptable salt thereof, and butylpyridinium is as shown in Formula 1 below.

[Formula 1]

As used herein, the term "derivative" means a chemical compound which is changed to such an extent that the structure and properties of the mother compound are not significantly changed by introducing a functional group to butylpyridinium, or substituting, oxidizing, or reducing a functional group of butylpyridinium, etc. For example, the alkyl group comprising 4 carbon atoms bonded to the butylpyridinium may be substituted with a functional group comprising an alkyl group comprising 4 or more carbon atoms. Specifically, it may be substituted with a functional group comprising 4 to 16 carbon atoms, and more specifically, with a functional group comprising 4, 12, or 16 carbon atoms, but is not limited thereto.

Specifically, the derivative may be dodecylpyridinium substituted with an alkyl group having 12 carbon atoms, as shown in Formula 2 below.

[Formula 2]

Further, the derivative may be cetylpyridinium substituted with an alkyl group having 16 carbon atoms, as shown in Formula 3 below.

[Formula 3]

The International Union of Pure and Applied Chemistry (IUPAC) name of the cetylpyridinium is 1-hexadecylpyridinium, and it may exist as a salt form reacted with hydrochloric acid, bromine, etc., such as cetylpyridinium chloride, cetylpyridinium bromide, etc., and is not limited thereto.

In the present invention, "cetylpyridinium", which is a derivative of butylpyridinium, is in the form of cetylpyridinium chloride, and it has been known to exhibit an excellent effect against periodontal diseases by sterilizing harmful bacteria in the oral cavity, but its relevance with the differentiation of myoblasts has not been known. In addition, butylpyridinium, dodecylpyridinium, etc. have not been known to be associated with the differentiation of myoblasts. Therefore, the present inventors first investigated that butylpyridinium, a derivative thereof, or a pharmaceutically acceptable salt thereof has the use of differentiating myoblasts, and thereby completed the present invention.

As used herein, the term "pharmaceutically acceptable salt" means a formulation of a chemical compound that does not cause serious irritations when administered to organisms and does not damage the biological activity and properties of the compound. The pharmaceutical salt may comprise an acid that forms a non-toxic acid-addition salt comprising a pharmaceutically acceptable anion, for example, an acid-addition salt formed by an inorganic acid such as hydrochloric acid, sulfuric acid, nitric acid, phosphoric acid, hydrobromic acid, hydriodic acid, etc.; by an organic carboxylic acid such as tartaric acid, formic acid, citric acid, acetic acid, trichloroacetic acid, trifluoroacetic acid, gluconic acid, benzoic acid, lactic acid, fumaric acid, maleic acid, salicylic acid, etc.; and by a sulfonic acid such as methanesulfonic acid, ethanesulfonic acid, benzenesulfonic acid, p-toluenesulfonic acid, etc. For example, the pharmaceutically acceptable carboxylic acid salt may comprise metal salts or alkaline earth metal salts formed by lithium, sodium, potassium, calcium, or magnesium, etc.; amino acid salts such as lysine, arginine, or guanidine, etc.; and organic salts such as dicyclohexylamine, N-methyl-D-glutamine, tris(hydroxymethyl)methylamine, diethanolamine, choline, and triethylamine, etc.

As a specific exemplary embodiment of the present invention, the salt may be butylpyridinium chloride, dodecylpyridinium chloride, cetylpyridinium chloride, butylpyridinium bromide, dodecylpyridinium bromide, or cetylpyridinium bromide, but is not limited thereto.

As used herein, the term "differentiation of myoblasts" is a process in which myoblasts, which are mononuclear, form a multinucleated myotube by fusion. Myoblasts which correspond to muscle precursor cells express a $Pax7^+$ marker in a case of self-renewal, and express a $Pax7^+/MyoD^+$ marker in a case of proliferation. Cells in a differentiation stage forming myotubes may be distinguished by using a $Pax7^-$ $MyoD^+$ $MyoG^+$ marker. Cells in the initial stage of differentiation forming the myotubes show an increase in the expression of myogenic transcription factors such as MyoD, and in the middle stage, the myogenin expression is increased. In the late stage when the differentiation is nearly finished, the expression of myosin heavy chain (MyHC) is increased.

Specifically, one exemplary embodiment of the present invention relates to a composition for promoting the differentiation of myoblasts comprising butylpyridinium, a derivative thereof, or a pharmaceutically acceptable salt thereof, at a concentration in a range from 0.001 μM to 5.0 μM. The composition may be a DMEM medium for differentiation comprising horse blood serum, but may comprise a culture medium or a composition capable of promoting the differentiation of myoblasts without limitation. The composition, more specifically, may comprise butylpyridinium, a derivative thereof, or a pharmaceutically acceptable salt thereof at a concentration in a range from 0.005 μM to 2.5 μM, and most specifically, from 0.01 μM to 0.5 μM. Also, the composition may further comprise additional materials necessary for cell culture or differentiation.

When butylpyridinium, a derivative thereof, or a pharmaceutically acceptable salt thereof is comprised at a concentration of less than 0.001 μM, the differentiation promoting effect may be reduced due to a low concentration, and when the concentration thereof is more than 5.0 μM, it is possible to cause toxicity.

Another exemplary embodiment of the present invention is a method for promoting the differentiation of myoblasts comprising treating myoblasts with butylpyridinium, a derivative thereof, or a pharmaceutically acceptable salt thereof. Butylpyridinium, a derivative thereof, or a pharmaceutically acceptable salt thereof is as described above. Specifically, the method for promoting the differentiation of myoblasts may promote the differentiation by treating myoblasts with cetylpyridinium, a derivative thereof, or a pharmaceutically acceptable salt thereof in vitro or in vivo.

Another exemplary embodiment of the present invention provides a method for preparing differentiated myoblasts comprising treating myoblasts with butylpyridinium, a derivative thereof, or a pharmaceutically acceptable salt to differentiate myoblasts.

Butylpyridinium, a derivative thereof, or a pharmaceutically acceptable salt thereof is as described above. The method of the present invention is characterized by preparing differentiated myoblasts comprising treating myoblasts with butylpyridinium, a derivative thereof, or a pharmaceutically acceptable salt in vitro or in vivo.

Figure 1:
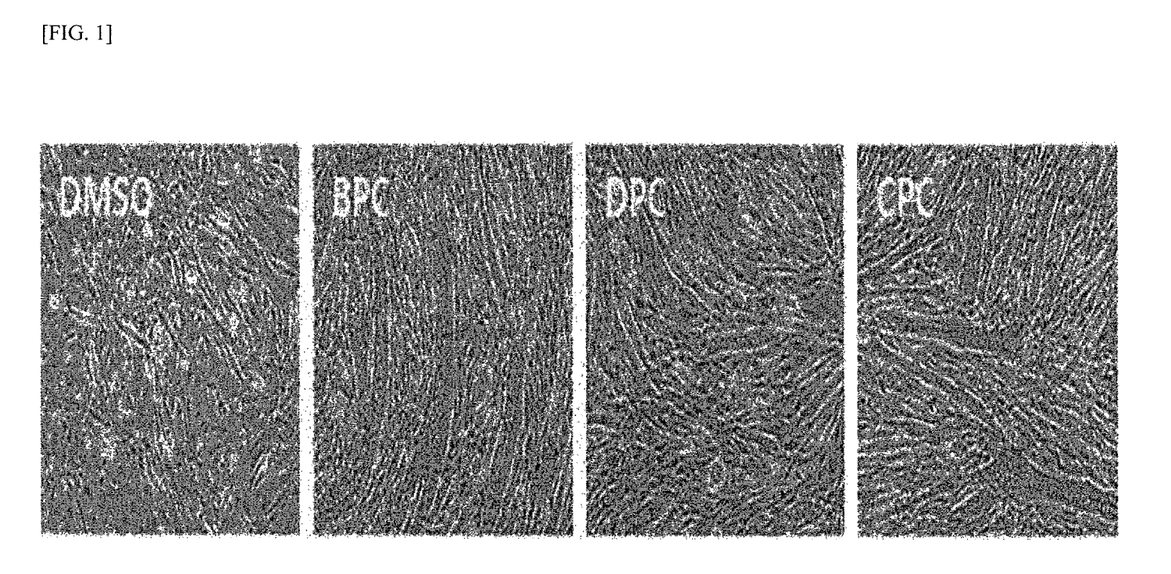
FIG. 1 shows the result confirming the differentiation of C2C12 myoblast cell lines treated with butylpyridinium chloride and its derivatives, cetylpyridinium chloride and dodecylpyridinium chloride, under phase contrast microscopy.
Figure 2:
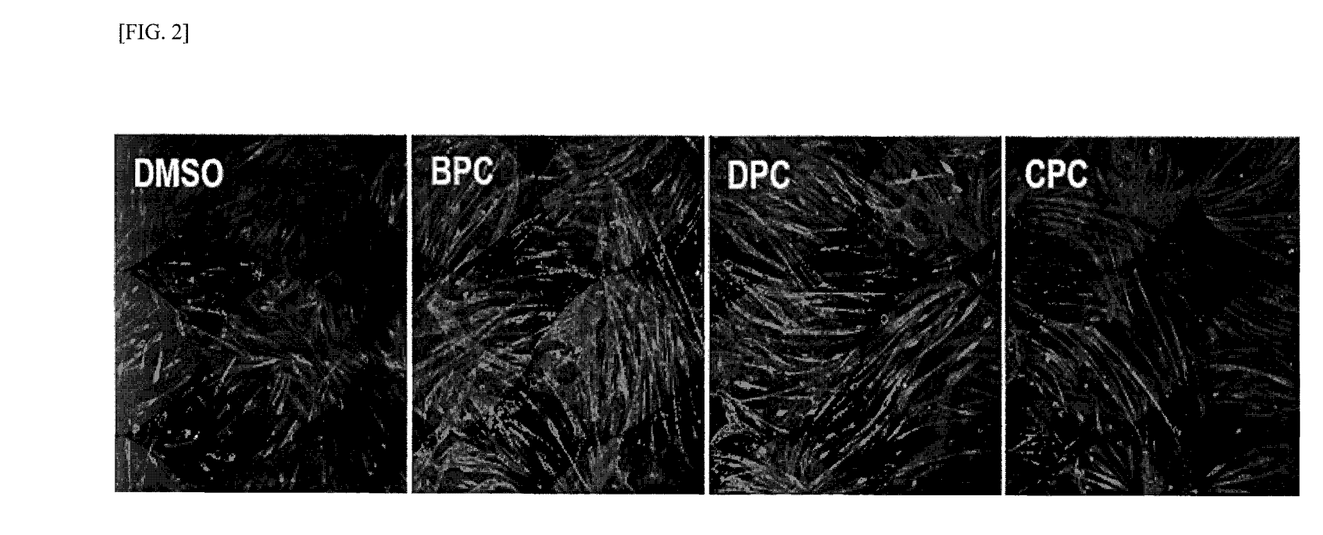
FIG. 2 shows the result confirming the differentiation of C2C12 myoblast cell lines treated with butylpyridinium chloride and its derivatives, cetylpyridinium chloride and dodecylpyridinium chloride, by immunocytochemistry.
Figure 3:
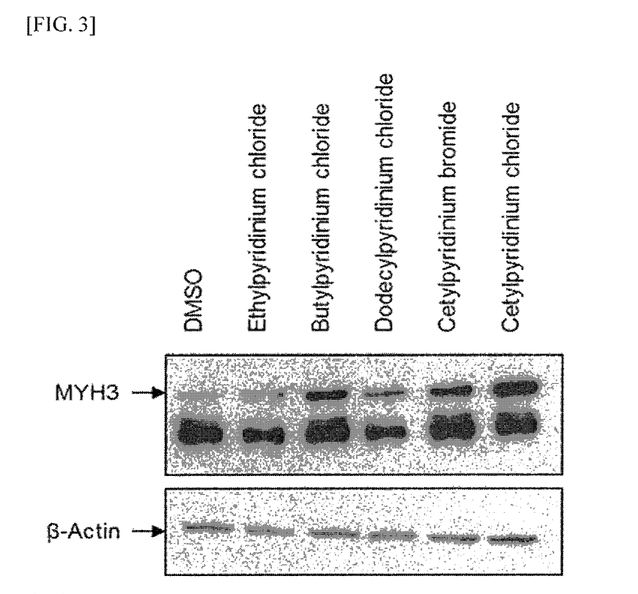
FIG. 3 shows the result confirming the expression of myosin heavy chain 3 (MYH3) in C2C12 myoblast cell lines, treated with ethylpyridinium chloride, butylpyridinium chloride, dodecylpyridinium chloride, cetylpyridinium chloride, and cetylpyridinium bromide, by Western blot.

In one example of the present invention, after treating myoblasts with each of cetylpyridinium chloride, butylpyridinium chloride, and dodecylpyridinium chloride at a concentration of 0.2 μM, the degree of differentiation was observed under phase contrast microscopy, it was confirmed that compared to the negative control group (DMSO), differentiation was promoted, thereby forming many myotubes (FIG. 1), and the effect of promoting the differentiation of muscle cells was confirmed to be very high by immunocytochemistry and Western blot (FIGS. 2 and 3).

Accordingly, the present invention is capable of forming myotubes and preparing differentiated myoblasts that express MYH3 protein in vitro or in vivo.

Another exemplary embodiment of the present invention relates to a pharmaceutical composition for preventing or treating a disease associated with muscle weakness comprising butylpyridinium, a derivative thereof, or a pharmaceutically acceptable salt thereof. The concentration of butylpyridinium, a derivative thereof, or a pharmaceutically acceptable salt thereof is as described above.

As used herein, the term "muscle weakness" means a condition in which the strength of one or more muscles is reduced. The muscle weakness may be limited to any one muscle, one side of the body, upper or lower limb, etc., or it may be displayed over the entire body. Furthermore, subjective symptoms of muscle weakness such as muscle fatigue or muscle pain may be quantified by an objective method through a physical examination.

The disease associated with muscle weakness in the present invention means any disease caused by muscle weakness and may be, for example, sarcopenia, muscular atrophy, muscular dystrophy, or acardiotrophy, but is not limited thereto.

Thus, the composition of the present invention may be used for preventing or treating sarcopenia, muscular atrophy, muscular dystrophy, or acardiotrophy through promoting the differentiation of myoblasts.

Specifically, sarcopenia of the present invention means a gradual reduction in the skeletal muscle mass, which directly causes a reduction in muscle strength, and as a result it means a condition where a reduction or a disorder of various body functions may occur.

Moreover, muscular atrophy means a condition in which the muscles of the limbs continue to shrink almost symmetrically, thereby causing progressive degeneration of motor nerve fibers and cells in the spinal cord, and thereby causing amyotrophic lateral sclerosis (ALS) and spinal progressive muscular atrophy (SPMA).

Muscular dystrophy is a disease exhibiting progressive muscular atrophy and muscle weakness, and pathologically, it refers to degenerative myopathy characterized by the necrosis of muscle fibers. Muscle weakness and muscular atrophy occur after going through the process of the necrosis and degeneration of muscle fibers due to damage to a myocyte membrane.

Acardiotrophy of the present invention refers to the atrophy of heart due to external or internal factors, and due to starvation, debilitating diseases, or senility, myocardial fibers become skinnier and thinner, and it may lead to a reduction of the adipose tissue and cause a symptom of the atrophy of the heart exhibiting a brown color.

As used herein, the term "prevention" means any activity suppressing a disease associated with muscle weakness or delaying the onset of the disease by the administration of the composition.

As used herein, the term "treatment" means any activity improving or ameliorating symptoms associated with muscle weakness by the administration of the composition.

The pharmaceutical composition of the present invention for administration comprises the butylpyridinium, derivative thereof, or pharmaceutically acceptable salt thereof, specifically butylpyridinium chloride, dodecylpyridinium chloride, cetylpyridinium chloride, butylpyridinium bromide, dodecylpyridinium bromide, or cetylpyridinium bromide, or pharmaceutically acceptable carriers, excipients, or diluents.

The carriers, excipients, and diluents may be lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline amorphous cellulose, polyvinylpyrrolidone, water, methyl hydroxybenzoate, propyl hydroxybenzoate, talc, magnesium stearate, and mineral oil.

The pharmaceutical composition of the present invention may be prepared as a pharmaceutical formulation using well-known methods in the art to provide a rapid, sustained, or delayed release of butylpyridinium, a derivative thereof, or a pharmaceutically acceptable salt thereof. In the preparation of formulations, it is desirable to either mix or dilute the active ingredient with a carrier, or enclose the active ingredient in a carrier in a container shape.

Further, the pharmaceutical composition of the present invention is applicable as any formulation, but it is desirable to be prepared for parenteral use. Parenteral formulations may be in a form for injection, external application, or in a spray form such as aerosols.

Formulations for parenteral administration include sterile aqueous solutions, non-aqueous solutions, suspensions, emulsions, lyophilized medicines, and suppositories. For a non-aqueous solvent, as a suspension, propylene glycol, polyethylene glycol, vegetable oil such as olive oil, and injectable esters such as ethyl oleate may be used.

In order to formulate into an injection formulation, butylpyridinium, a derivative thereof, or a pharmaceutically acceptable salt may be mixed with a stabilizer or a buffer in water to be prepared as a solution or a suspension, and it may be formulated as a unit dosage use in an ampoule or a vial.

The pharmaceutical composition of the present invention comprising butylpyridinium, a derivative thereof, or a pharmaceutically acceptable salt thereof may be directly administered to a region of a subject with a disease associated with muscle weakness or of a subject at risk for the development of the disease, or after preparing differentiated myoblasts by applying the composition to myoblasts in vitro or in vivo, the differentiated myoblasts may be administered to a region where muscle strengthening is needed in a subject with a disease associated with muscle weakness or a subject at risk for the development of the disease.

Further, the composition may comprise additional components such as compounds already known to be medicines to treat a disease associated with muscle weakness, where butylpyridinium, a derivative thereof, or a pharmaceutically acceptable salt thereof does not interfere with the prevention or treatment of the disease associated with muscle weakness.

Specifically, the pharmaceutical composition of the present invention is characterized by promoting the differentiation of myoblasts. In one example of the present invention, after treating myoblasts with each of cetylpyridinium chloride, butylpyridinium chloride, and dodecylpyridinium chloride at a concentration of 0.2 µM, the degree of differentiation was observed under phase contrast microscopy, and it was confirmed that, compared to the negative control group (DMSO), differentiation was promoted, thereby forming many myotubes (FIG. 1), and the effect of promoting the differentiation of muscle cells was confirmed to be very high by immunocytochemistry and Western blot (FIGS. 2 and 3). In addition, the tibialis anterior muscle was immobilized for 3 days (muscle immobilization), thereby inducing muscle damage. Thereafter, the muscle was released from immobilization and was allowed to be regenerated. Through conducting the same motor ability improvement tests after seven days, in the experimental groups to which butylpyridinium chloride or cetylpyridinium chloride was administered, it was confirmed that the range of decrease in the grip strength was reduced (FIGS. 4 and 7), the motor ability to maintain the sense of balance was improved (FIGS. 5 and 8), and the endurance was improved (FIGS. 6 and 9), compared to the control group.

Figure 11:
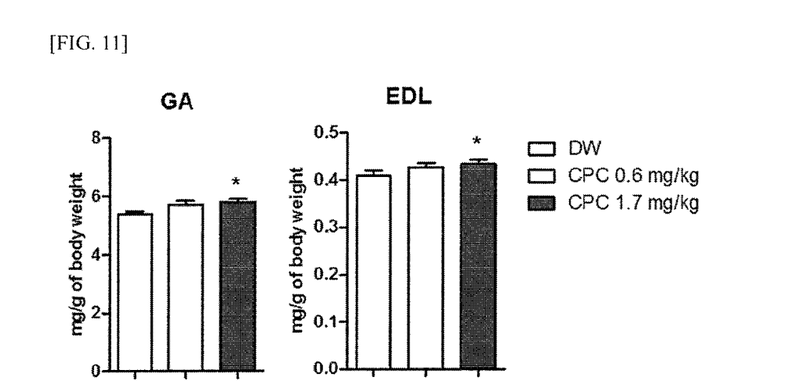
FIG. 11 shows the comparison of the increasing effects of the skeletal muscle mass of mice due to the treatment of cetylpyridinium chloride, before and after muscle immobilization periods.
Figure 12:
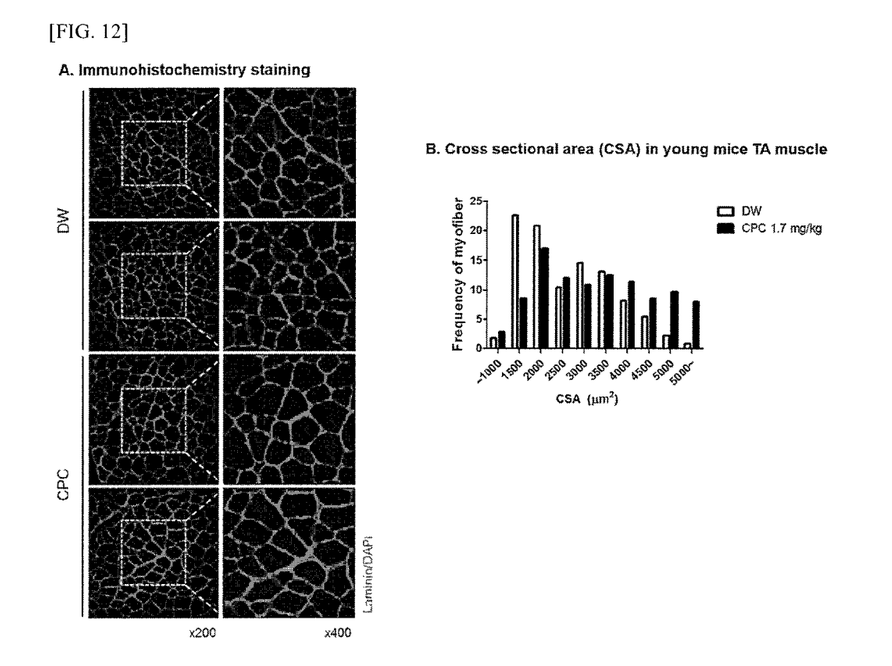
FIG. 12 shows the comparison of the increasing effects of the muscle cross-sectional area of mice due to the treatment of cetylpyridinium chloride, before and after muscle immobilization periods.
Figure 14:
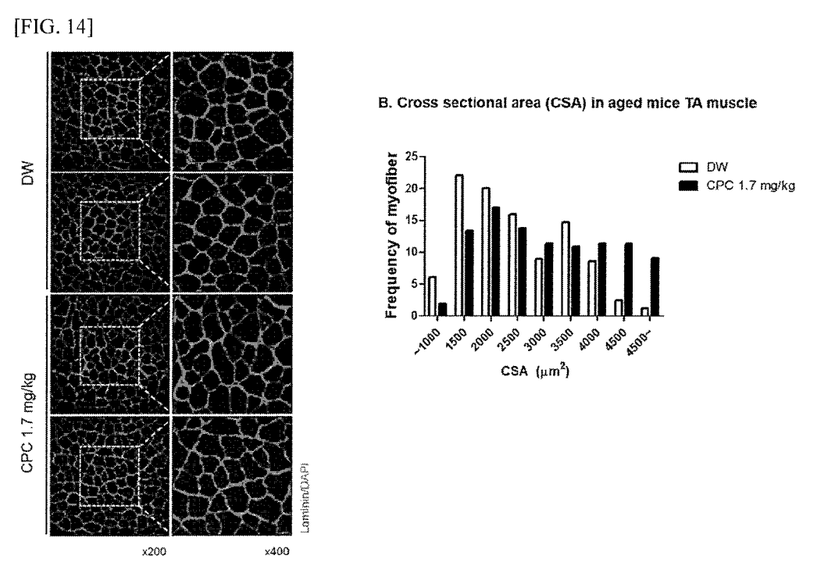
FIG. 14 shows the comparison of the increasing effects of the muscle cross-sectional area of aged mice due to the treatment of cetylpyridinium chloride, before and after muscle immobilization periods.
Figure 15:
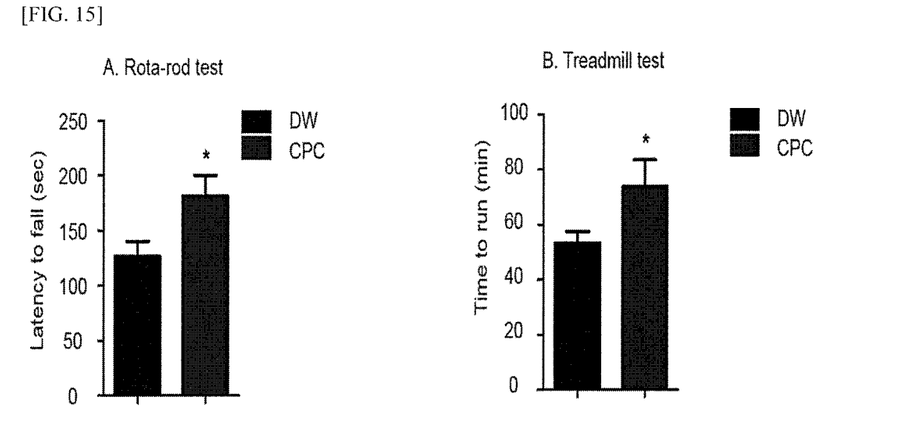
FIG. 15 shows the comparison of the improving effects of the balance ability and endurance of the MDX mice due to the treatment of cetylpyridinium chloride, before and after muscle immobilization periods.

Further, in another example of the present invention, as a result of confirming the effect of strengthening muscles in the mouse, it was confirmed that cetylpyridinium chloride, in a concentration-dependent manner, exhibited effects of improving the sense of balance and endurance (FIG. 10), increasing skeletal muscle mass (FIG. 11), and increasing the muscle cross-sectional area (FIG. 12). As another exemplary embodiment of the present invention, it was confirmed that the cetylpyridinium chloride, in a concentration-dependent manner, exhibited an effect of improving muscle strength in aged mouse (FIGS. 13 and 14), and it was confirmed that motor ability was improved in a Duchenne muscular dystrophy model mouse (FIG. 15).

Through these results, it was shown that butylpyridinium, a derivative thereof, or a pharmaceutically acceptable salt thereof was effective at promoting the differentiation of myoblasts, and it is useful for preventing or treating a disease associated with muscle weakness.

Another exemplary embodiment of the present invention relates to a food composition for preventing or ameliorating a disease associated with muscle weakness comprising butylpyridinium, a derivative thereof, or a sitologically acceptable salt. The composition of the present invention may be used in order to prevent or ameliorate a disease associated with muscle weakness, before the development of the disease or after the onset of the disease, at the same or separate time with another medicine for the treatment of the disease. The concentration of butylpyridinium, a derivative thereof, or a sitologically acceptable salt thereof is as described above.

The disease associated with muscle weakness means all of the diseases that may be caused by muscle weakness, for example, sarcopenia, muscular atrophy, muscular dystrophy, or acardiotrophy, but is not limited thereto. Preferably, the food composition is characterized by promoting the differentiation of myoblasts.

As used herein, the term "ameliorating" means all of the activities of, for example, at least reducing parameters associated with the condition being treated, for example, reducing the severity of the symptom.

Also, when the food composition of the present invention is used as a food additive, the composition may be directly added or used with other food or food ingredients, and may be appropriately used according to conventional methods. In general, during the manufacture of food or beverage, the composition of the present invention may be added, compared to the raw material, in an amount of less than 15 wt %, preferably less than 10 wt %. However, for the purposes of health and hygiene, or in the case of long-term intake for the purpose of controlling health, the amount may be less than the range, and since there is no problem in terms of safety, the active ingredient may be used in an amount over the range.

The types of the food do not have any particular limitation. Examples of the food that may comprise the composition include meat, sausage, bread, chocolate, candy, snacks, confectionaries, pizza, ramen, other noodles, gums, dairy products including ice cream, various soups, beverages, tea, drinks, alcoholic beverages, and vitamin complexes, etc., including all of the health foods in the conventional sense.

The health beverage compositions of the present invention may include additional ingredients such as various flavors or natural carbohydrates. The natural carbohydrates mentioned above may be a monosaccharide such as glucose and fructose, a disaccharide such as maltose and sucrose, and natural sweeteners such as dextrin and cyclodextrin; and synthetic sweeteners such as saccharin, aspartame, etc. The ratio of the natural carbohydrate may be appropriately decided by those skilled in the art.

Besides the above, the composition of the present invention may comprise various nutritional supplements, vitamins, electrolytes, flavoring agents, coloring agents, pectic acid and a salt thereof, alginic acid and a salt thereof, organic acids, protective colloid thickeners, pH modifiers, stabilizers, preservatives, glycerin, alcohols, carbonating agents used in carbonated drinks, etc. Other compositions of the present invention may comprise fruit chunks for preparing natural fruit juice, fruit juice beverages, and vegetable beverages. These components may be used alone or in combination. The ratio of these additives may also be appropriately decided by those skilled in the art.

Another exemplary embodiment of the present invention relates to a composition for strengthening muscles comprising butylpyridinium, a derivative thereof, or a pharmaceutically acceptable salt thereof.

Further, another exemplary embodiment of the present invention relates to a composition for strengthening muscles comprising butylpyridinium, a derivative thereof, or a sitologically acceptable salt thereof.

As used herein, the term "muscle strengthening" means strengthening the body performance, strengthening the maximum endurance, increasing skeletal muscle mass, strengthening of muscle recovery, reducing muscle fatigue, improving, energy balance, or any combination effect thereof.

The composition for strengthening muscles of the present invention comprising butylpyridinium, a derivative thereof, or a pharmaceutically or sitologically acceptable salt thereof is capable of increasing the total skeletal muscle mass through its ability to differentiate myoblasts into myocytes, which increases the skeletal muscle mass, and is capable of strengthening maximum endurance, thereby strengthening the body performance and reducing muscle fatigue. Further, because myocytes may be replaced rapidly, muscle damage may be healed quickly.

In order to administer the composition for strengthening muscles of the present invention, the composition for strengthening muscles may comprise, in addition to the butylpyridinium, a derivative thereof, or a pharmaceutically or sitologically acceptable salt thereof, pharmaceutically acceptable carriers, excipients, or diluents. The pharmaceutically acceptable carriers, excipients, or diluents are as described above.

Further, the composition for strengthening muscles of the present invention may be prepared in the form of a food composition or a food additive, and particularly in the form of a health food composition. Therefore, the composition for strengthening muscles of the present invention may be used, not only for the reduction of muscle due to aging, but also in the form of a supplement for muscle generation and muscle strengthening for normal individuals, etc.

In one example of the present invention, by treating a mouse with each of the cetylpyridinium chloride and butylpyridinium chloride, thereafter by conducting the grip strength tests, rota-rod tests, and treadmill tests, it was confirmed that the compositions can be used for strengthening muscles by confirming the effect of improving muscle strength.

Another exemplary embodiment of the present invention relates to a feed or a feed additive for strengthening muscles, comprising butylpyridinium, a derivative thereof, or a pharmaceutically acceptable salt thereof.

As used herein, the term "feed" means a substance that supplies organic or inorganic nutrients necessary for the maintenance of life for animals. The feed may supply energy and nutrients such as proteins, lipids, vitamins, minerals, etc. that are required by animals such as domestic animals, and may be plant-based feeds such as grains, nuts, food by-products, algae, fibers, fat and oils, starch, meal, grain by-products, etc., or may be animal-based feeds such as proteins, inorganic substances, fat and oils, minerals, single-cell proteins, etc., but is not limited thereto.

As used herein, the term "feed additive" means a substance to be added to a feed to improve the productivity and the health of an animal, and in particular, although it is not limited thereto, it may additionally comprise amino acids, vitamins, enzymes, flavoring agents, silicate agents, buffering agents, extracting agents, oligosaccharides, etc.

The content of the butylpyridinium, a derivative thereof, or a pharmaceutically acceptable salt thereof comprised in the feed or feed additive for strengthening muscles may be in a range from 0.001% (w/w) to 1% (w/w), specifically from 0.005% (w/w) to 0.9% (w/w), and more specifically, from 0.01% (w/w) to 0.5% (w/w), but is not particularly limited thereto.

Another exemplary embodiment of the present invention relates to a method for treating a disease associated with muscle weakness, comprising administering butylpyridinium, a derivative thereof, or a pharmaceutically acceptable salt thereof to a subject in need thereof.

The diseases associated with muscle weakness mean all of the diseases that may be caused by muscle weakness and may be, for example, sarcopenia, muscular atrophy, muscular dystrophy, or acardiotrophy, but is not limited thereto.

MODE OF THE INVENTION

Hereinafter, the present invention will be described in more detail with accompanying exemplary embodiments. However, the exemplary embodiments disclosed herein are only for illustrative purposes and should not be construed as limiting the scope of the present invention.

Example 1. Culture of C2C12 Myoblast Cell Line

C2C12 is a cell line of myoblasts obtained from a C3H strain live mouse, and it is widely used in the differentiation studies of myoblasts.

The above-described C2C12 cells were cultured in each of general media for cell growth and media for differentiation. In the normal cell growth media (GM), DMEM supplemented with 10% fetal bovine serum was used, and in the differentiation media (DM), DMEM containing 2% horse blood serum was used.

Example 2. Differentiation of Myoblasts

After aliquoting cells in cell culture media and culturing for 24 hours, the cultured cells were treated with each of DMSO, cetylpyridinium chloride (0.2 µM), butylpyridinium chloride (0.2 µM), and dodecylpyridinium chloride (0.2 µM) in each differentiation medium, and were induced to differentiate for 3 days. The DMSO, cetylpyridinium chloride, butylpyridinium chloride, and dodecylpyridinium chloride used in the experiment were all purchased from Sigma-Aldrich.

Example 3. Promotion of Myoblast Differentiation by Butylpyridinium Chloride or a Derivative Thereof (In Vitro)

3-1. Phase Contrast Microscopy

In order to confirm the formation of many myotubes by treating myoblasts with each of butylpyridinium chloride and its derivatives (i.e., cetylpyridinium chloride and dodecylpyridinium chloride), C2C12 cells on a cover glass coated with 0.1% gelatin were differentiated for 3 days while treating with each of DMSO, which is a drug carrier, butylpyridinium chloride, cetylpyridinium chloride, and dodecylpyridinium chloride, at a concentration of 0.2 µM, and were observed under phase contrast microscopy. According to the experimental results, compared to DMSO, which is the control group, when each of butylpyridinium chloride, cetylpyridinium chloride, and dodecylpyridinium chloride was treated, more myotubes were formed, thereby confirming the differentiation promoting effect (×100) (FIG. 1).

3-2. Immunocytochemistry

C2C12 cells on a cover glass coated with 0.1% gelatin were differentiated for 3 days. After washing the cells with 1×PBS, fixing with 3.7% paraformaldehyde at room temperature for 15 minutes, and washing 3 times with 1×PBS, a permeabilization buffer was added, and the cells were reacted at room temperature for 15 minutes. After washing the cells three times with 1×PBS again, the cells were reacted for 30 minutes with PBST (blocking buffer, PBS containing 0.5% Tween 20) containing 1% BSA to deter any unspecific binding of antibodies. The primary antibody against MYH3 (SC-20641, Santa Cruz Biotechnology) was added to the blocking buffer by diluting at a ratio of 1:500 and was reacted at room temperature for 1 hour. After washing the cells three times with 1×PBS, the secondary antibody (Goat anti-Rabbit IgG-HRP), which was diluted in the blocking buffer at a ratio of 1:5000, was added and reacted at room temperature for 1 hour, and the cells were washed three times with 1×PBS. The cover glass was placed on a slide glass, photographs were taken with a fluorescence microscope, and the results were analyzed.

In the present invention, after each of DMSO (negative control group), butylpyridinium chloride, cetylpyridinium chloride, and dodecylpyridinium chloride was treated to induce the differentiation of the C2C12 cell line, on the third day, in order to compare the degree of differentiation of the myoblasts, after staining with an antibody against MYH3, the expression of the protein was confirmed. As a result, the expression of MYH3 was confirmed to be very high after each of butylpyridinium chloride, cetylpyridinium chloride, and dodecylpyridinium chloride was treated at a concentration of 0.2 µM (FIG. 2).

3-3. Western Blot

After aliquoting the C2C12 cells in the culture media and culturing for 24 hours, each of DMSO (control group), ethylpyridinium chloride, butylpyridinium chloride, dodecylpyridinium chloride, cetylpyridinium chloride, and cetylpyridinium bromide was applied to each culture medium at a concentration of 0.2 µM every day, and differentiation was induced. The cells were harvested on the third day of differentiation and centrifuged at 1200 rpm for 3 minutes. After adding 100 µL of a lysis buffer to the cells, the cells were sonicated and centrifuged at 3000 rpm for 10 minutes to obtain a water-soluble protein, and after adding a 4× sample buffer, the cells were reacted in boiling water for 5 minutes.

10 μg of the protein was loaded on a 12% SDS-PAGE gel and developed, and then was transferred onto a nitrocellulose membrane. The nitrocellulose membrane was blocked in 5% skim milk for 1 hour at room temperature and washed 5 times with TTBS (0.03% Tween 20, Tris 2.42 g, NaCl 9 g, pH 7.4, and 1 L) for 5 minutes each. The primary antibody was diluted in TTBS containing 5% skim milk at a ratio of 1:500 and was added to the nitrocellulose membrane, and after reacting at room temperature for 2 hours, the nitrocellulose membrane was again washed 5 times with TTBS for 5 minutes each. The secondary antibody was diluted at a ratio of 1:5000 again in TTBS containing 5% skim milk and added, was reacted at room temperature for 2 hours, was washed with TTBS 5 times for 5 minutes each, and ECL (Enhanced Chemiluminescent solution, Pierce) was added. Thereafter, the membrane was exposed to X-ray film, and the amount of the protein was measured.

As a result of the above experiments, it was confirmed that the amount of the MYH3 protein contained in the same amount of protein was significantly increased in groups treated with each of cetylpyridinium chloride, butylpyridinium chloride, and dodecylpyridinium chloride. The MYH3 expression due to the DMSO treatment in the control group was insignificant, but the MYH3 expression was increased by cetylpyridinium chloride, butylpyridinium chloride, and dodecylpyridinium chloride. In addition, when treated with cetylpyridinium bromide, it was confirmed that the MYH3 expression was increased (FIG. 3).

This indicated that the amount of the myosin protein contained in the same amount of protein was rapidly increased by cetylpyridinium chloride, butylpyridinium chloride, and dodecylpyridinium chloride, and it was found that the effect of promoting the differentiation of myoblasts by butylpyridinium chloride, dodecylpyridinium chloride, cetylpyridinium chloride, and cetylpyridinium bromide was very high.

However, in the case of ethylpyridinium chloride, which is one of derivatives of butylpyridinium chloride and has two carbon skeletons, the protein of MYH3 did not increase, unlike other derivatives. From this result, it was found that among derivatives of butylpyridinium, only the derivatives that have four or more carbon skeletons were effective.

Example 4. Confirmation of Improvement in Motor Ability of Animals by Muscle Regeneration after Administration of Butylpyridinium Chloride As experimental animals, 20 of C57BL/6 male mice aged 6 weeks were used. The experimental animals were assigned to two groups: a control group, to which 10 mice having similar weights were assigned without administration, and an experimental group, to which 10 mice having similar weights were assigned with butylpyridinium chloride administration.

Butylpyridinium chloride was dissolved in distilled water to be prepared at a concentration of 15 mg/kg and orally administered to mice in the experimental group. It was also administered continuously during the muscle immobilization periods described below.

In this experiment, as a method for inducing muscle regeneration in mice, the tibialis anterior muscle immobilization protocol was used. In this method, the thighs and shins of one leg of a mouse were fixed using a medical staple so that legs were immobilized, and after leaving the immobilized mouse alone for 3 days, the fixed leg was released. The principle used in this method is that when a leg is placed in a cast and the muscle of the leg is immobilized (i.e., not frequently used), the muscle is lost. It is a method for inducing muscle regeneration, in which, after the muscle loss due to immobilizing the shin muscle, the muscle is regenerated by releasing the immobilized muscle so that the muscle may move again. In this experiment, muscle damage was induced by immobilizing the tibialis anterior muscle for 3 days (muscle immobilization), and by releasing the muscle again, the muscle was allowed to be regenerated, and after 7 days, the same motor ability improvement tests were conducted.

4-1. Grip Strength Test

Grip strength was measured using a grip strength measuring instrument made by the company BIOSEB. The mouse was placed on a wire mesh attached to the instrument panel that can monitor the strength of a force, and the force of holding the wire mesh by the mouse while the tail was gripped downward was measured. The average value obtained after repeating the test 5 times consecutively was used.

Figure 4:
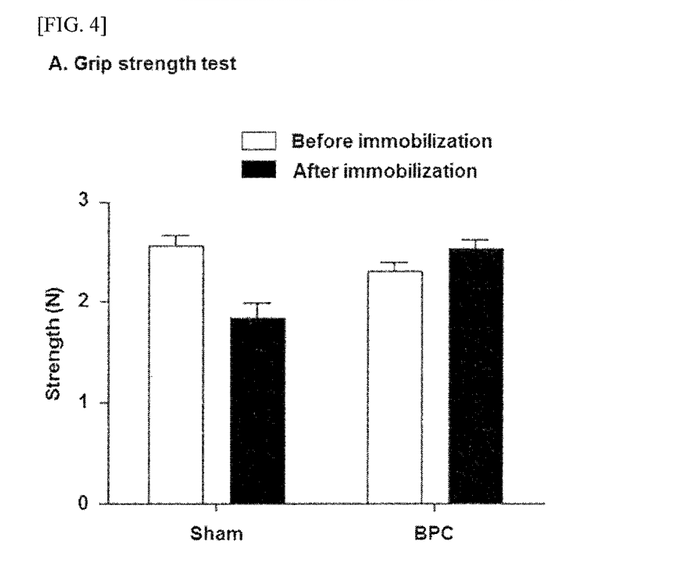
FIG. 4 shows the comparison of the improving effects of the grip strength of mice due to the treatment of butylpyridinium chloride, before and after muscle immobilization periods.

As a result of measuring the grip strength, it was confirmed that in the experimental group to which butylpyridinium chloride was administered, the range of decrease in the grip strength after the muscle immobilization was reduced compared to the control group (FIG. 4).

4-2. Rota-Rod Test

The exercise was applied using a rota-rod device consisting of 6 partitions (with a diameter of 7 cm, at an interval of 15 cm) and a rotatable cylindrical bar (with a height of 60 cm). Starting at a rotation speed of 10 rpm and accelerating to a speed of up to 40 rpm for 5 minutes, the time that the mouse did not fall from and remain on the rota-rod was measured. The average value displayed was measured after repeating 3 times the process of making the mouse rest for 15 minutes and making the mouse exercise.

Figure 5:
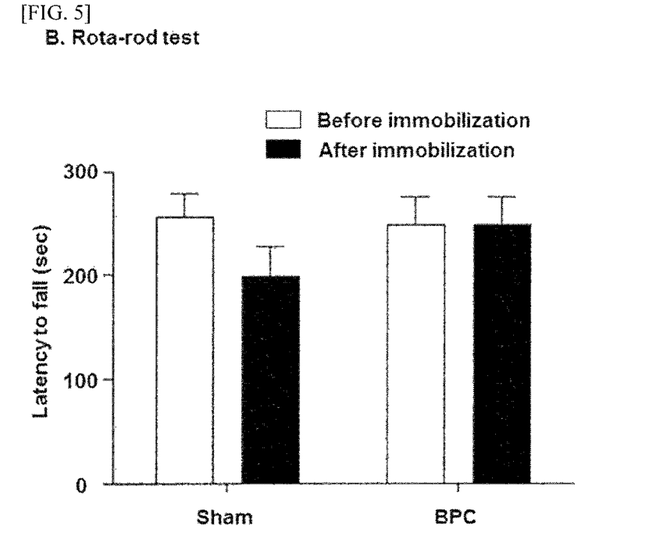
FIG. 5 shows the comparison of the improving effects of the balance ability of mice due to the treatment of butylpyridinium chloride, before and after muscle immobilization periods.

As a result of the rota-rod measurements, it was confirmed that the motor ability to maintain the sense of balance was improved in the experimental group with the administration of butylpyridinium chloride after muscle immobilization, compared to the control group (FIG. 5).

4-3. Treadmill Test

For the treadmill used in this test, a self-manufactured device was used. After each mouse was placed in an isolated lane and made to run, the time from the starting point to a point when the mouse was exhausted (i.e., judged to have no will to run) was recorded. The mouse was judged to be exhausted if the time that it did not run and stayed outside a lane was 10 seconds or more, and the time was recorded. In this experiment, repeated experiments on the same mouse could not be performed. The mouse was placed on the device and was made to run at a speed of 8 rpm, the speed was accelerated by 2 rpm every 10 minutes up to a speed of 18 rpm, and starting with no inclination, the inclination was increased by 5 degrees every 30 minutes.

Figure 6:
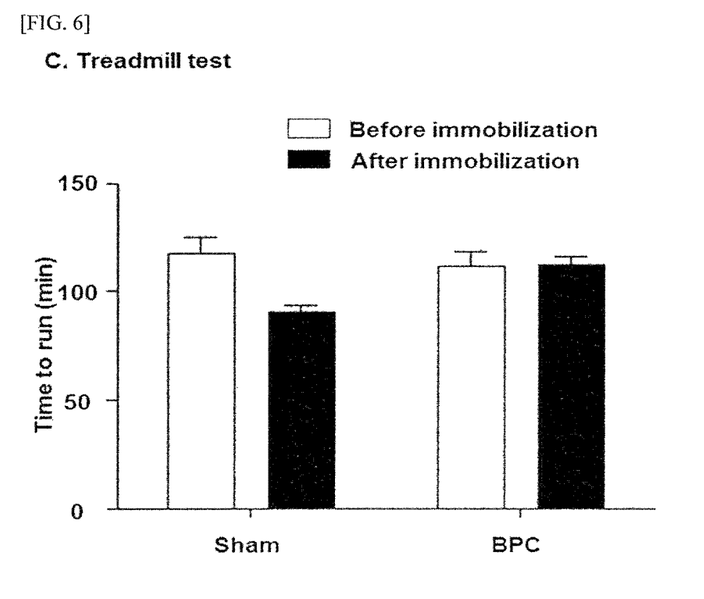
FIG. 6 shows the comparison of the improving effects of the endurance of mice due to the treatment of butylpyridinium chloride, before and after muscle immobilization periods.

As a result of the treadmill measurements, in the experimental group with the administration of butylpyridinium chloride, it was apparent that endurance was improved after muscle immobilization, compared to the control group (FIG. 6).

In the control group, it was confirmed that the motor ability was lowered after muscle immobilization in the grip strength, rota-rod, and treadmill tests, compared to before muscle immobilization. However, in the experimental group with the administration of butylpyridinium chloride, it was confirmed that the motor ability was not reduced; rather, it was maintained or improved compared to the control group.

Example 5. Improvement of Motor Ability of Animals by Muscle Regeneration after Administration of Cetylpyridinium Chloride, a Derivative of Butylpyridinium Chloride In order to confirm that a derivative having a structural correlation with butylpyridinium chloride showed the same effect, cetylpyridinium chloride was orally administered to 20 of C57BL/6 male mice at a concentration of 50 mg/kg for 2 weeks, and the improvement of the motor ability before and after muscle immobilization was confirmed.

5-1. Grip Strength Test

Figure 7:
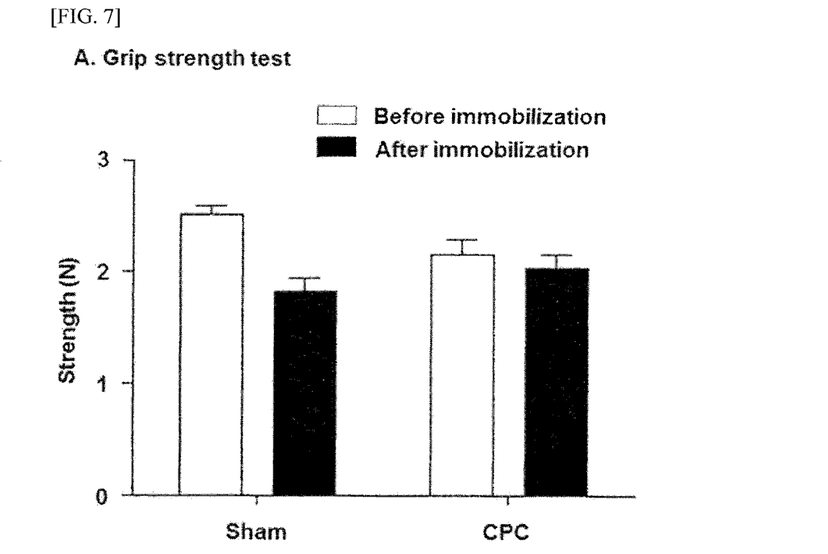
FIG. 7 shows the comparison of the improving effects of the grip strength of mice due to the treatment of cetylpyridinium chloride, before and after muscle immobilization periods.

The test was conducted in the same method as in Example 4-1 above, and after cetylpyridinium chloride was administered, it was confirmed that the range of decrease in grip strength, was reduced after muscle immobilization, compared to the control group (FIG. 7).

5-2. Rota-Rod Test

Figure 8:
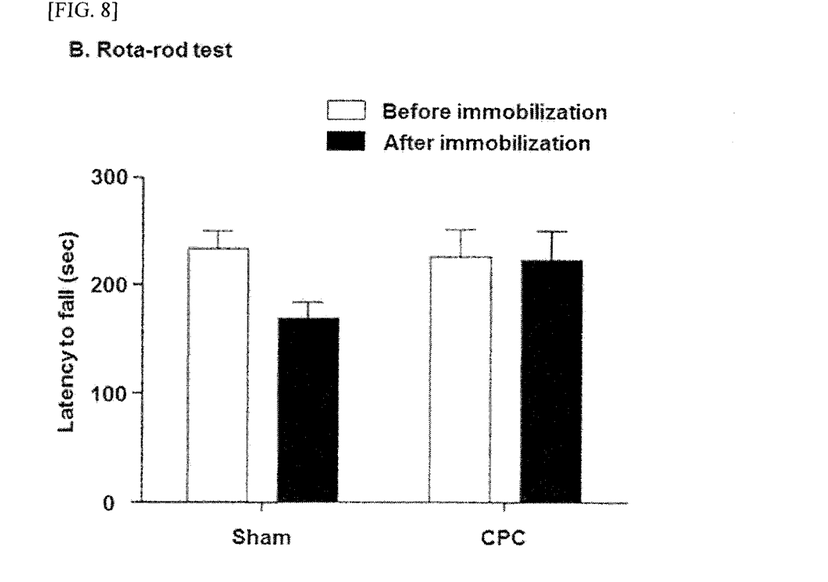
FIG. 8 shows the comparison of the improving effects of the balance ability of mice due to the treatment of cetylpyridinium chloride, before and after muscle immobilization periods.

The test was conducted in the same method as in Example 4-2 above, and after cetylpyridinium chloride was administered, it was confirmed that the motor ability to maintain the sense of balance was improved compared to the control group (FIG. 8).

5-3. Treadmill Test

Figure 9:
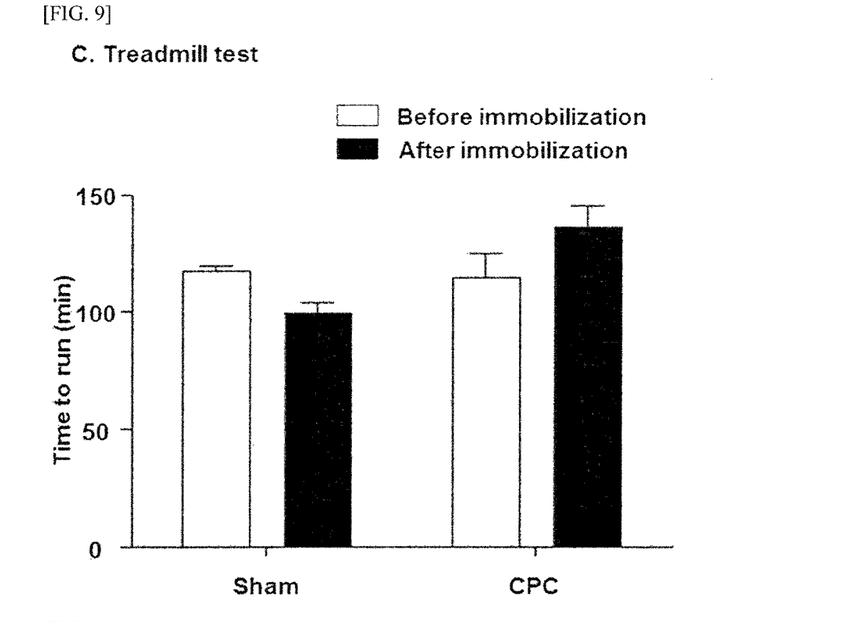
FIG. 9 shows the comparison of the improving effects of the endurance of mice due to the treatment of cetylpyridinium chloride, before and after muscle immobilization periods.

The test was conducted in the same method as in Example 4-3 above, and after cetylpyridinium chloride was administered, it was confirmed that endurance was improved compared to the control group (FIG. 9).

These results support that not only butylpyridinium chloride, but also the derivatives thereof have the same differentiation effect for muscle cells, and further the derivatives thereof have the effect of preventing or treating diseases associated with muscle weakness.

Figure 10:
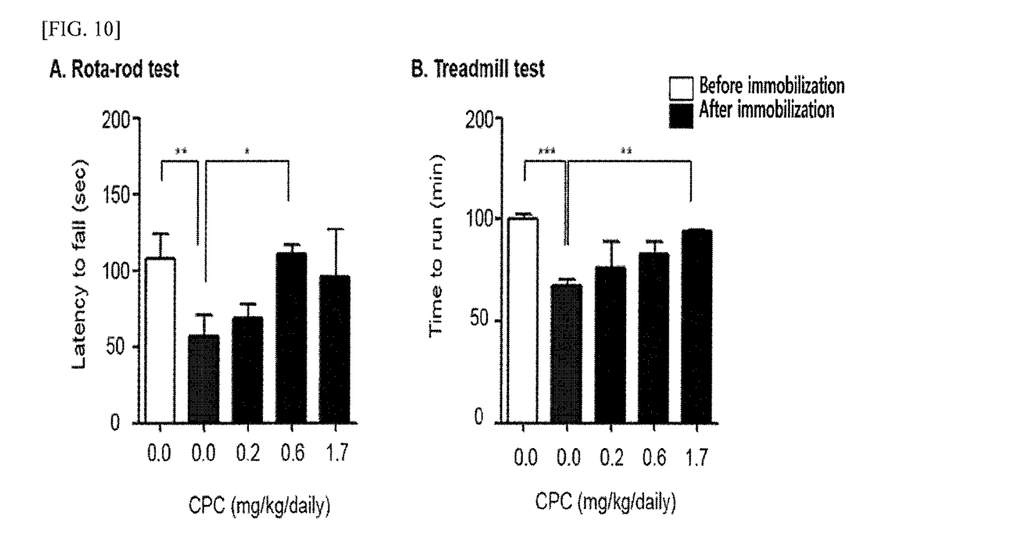
FIG. 10 shows the comparison of the improving effects of the balance ability and endurance of mice due to the dose-dependent treatment of cetylpyridinium chloride, before and after muscle immobilization periods.

Example 6. Improvement of Motor Ability of Animals by Muscle Regeneration after Concentration-Dependent Oral Administration of Cetylpyridinium Chloride, a Derivative of Butylpyridinium Chloride Cetylpyridinium chloride was orally administered in a concentration-dependent manner to mice in the mouse immobilization model. The motor ability was confirmed by the rota-rod and treadmill tests through the same methods as in Examples 4-2 and 4-3 (FIG. 10).

As a result, it was found that the motor ability was improved by cetylpyridinium chloride in a concentration-dependent manner.

Example 7. Confirmation of Increase in Skeletal Muscle Mass and Muscle Cross-Sectional Area by Muscle Regeneration after Concentration-Dependent Oral Administration of Cetylpyridinium Chloride, a Derivative of Butylpyridinium Chloride After cetylpyridinium chloride was orally administered to mice in the mouse immobilization model, in order to observe an increase in the skeletal muscle mass depending on the concentration of cetylpyridinium chloride, each mouse was immobilized, and 7 days after inducing regeneration, the mouse which finished the motor ability improvement tests was sacrificed, and the muscles of gastrocnemius (GA) and extensor digitorum longus (EDL) were separated. Afterwards, an increase in the skeletal muscle mass due to the drug was confirmed by dividing the weight of the separated muscle by the body weight of the mouse (FIG. 11).

As a result, after orally administering cetylpyridinium chloride to mice in the mouse immobilization model, it was found that the skeletal muscle masses of the gastrocnemius muscle and EDL muscle were increased by cetylpyridinium chloride in a concentration-dependent manner.

In addition, after orally administering cetylpyridinium chloride to mice in the mouse immobilization model, in order to observe that the muscle cross-sectional area was increased depending on the concentrations of cetylpyridinium chloride, each mouse was immobilized, and 7 days after inducing regeneration, the mouse which finished the motor ability improvement tests was sacrificed, and the tibialis anterior (TA) muscle was separated. The separated muscle was cut to a thickness of 5 $\mu$M and stained by immunofluorescence using a Laminin antibody. Laminin, which is the basis of the network of proteins between most cells and tissues, is an extracellular matrix glycoprotein formed in the basement membrane. By using the Laminin antibody, sections of the skeletal muscle fibers formed in the basement membrane were stained, and the cross-sectional area of the muscle fibers was measured (FIG. 12).

As a result, after orally administering cetylpyridinium chloride to mice in the mouse immobilization model, it was confirmed that the cross-sectional area of the muscle was increased in the group that was fed with cetylpyridinium chloride at a concentration of 1.7 mg/kg (mouse), compared to the control group.

Figure 13:
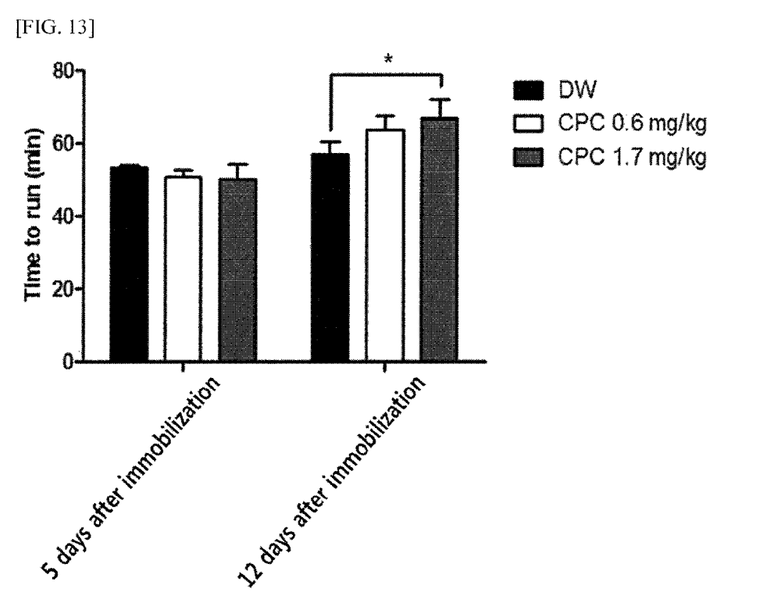
FIG. 13 shows the comparison of the improving effects of the endurance of aged mice due to the treatment of cetylpyridinium chloride, before and after muscle immobilization periods.

Example 8. Confirmation of Increase in Motor Ability and Muscle Cross-Sectional Area of Aged Animals by Muscle Regeneration after, Concentration-Dependent Oral Administration of Cetylpyridinium Chloride, a Derivative of Butylpyridinium Chloride In the mouse immobilization model of aged mice, in order to observe an increase in the motor ability depending on the concentrations of cetylpyridinium chloride after oral administration of cetylpyridinium chloride, cetylpyridinium chloride was orally administered in a concentration-dependent manner to 20-month-old male C57BL/6 aged mice, and the mice were immobilized. After 3 days of immobilization, the motor ability was confirmed using the treadmill tests which were conducted after 5 days and 12 days (FIG. 13).

As a result, even in the mouse immobilization model of 20-month-old male aged mice after oral administration of cetylpyridinium chloride, it was confirmed that the motor ability was improved in the group that was fed with cetylpyridinium chloride depending on the concentration thereof, compared to the control group.

Further, in order to observe that the cross-sectional area of the muscle was increased depending on the concentration of cetylpyridinium chloride after oral administration of cetylpyridinium chloride, 20-month-old C57BL/6 aged mice were orally administered with cetylpyridinium chloride and were immobilized. After 3 days of immobilization, the mice were sacrificed after 12 days after confirming the motor ability. The tibialis anterior (TA) muscle of the sacrificed mice was separated. The separated muscle was cut to a thickness of 5 $\mu$M and stained by immunofluorescence using the Laminin antibody to stain a section of skeletal muscle fibers formed in the basement membrane, and the cross-sectional area of the muscle fibers was measured (FIG. 14).

As a result, in the model where 20-month-old male aged mice were immobilized, as a result of oral administration of cetylpyridinium chloride, it was confirmed that the cross-sectional area of the muscle in the group that was fed with cetylpyridinium chloride at a concentration of 1.7 mg/kg (mouse) was increased compared to the control group.

Example 9. Confirmation of Improvement of Motor Ability of Animals with Duchenne Muscular Dystrophy after Administration of Cetylpyridinium Chloride, a Derivative of Butylpyridinium Chloride 6-month-old male MDX mice were orally administered cetylpyridinium chloride at a concentration of 1.7 mg/kg (mouse) for 4 weeks. The MDX mice are the model animal for Duchenne muscular dystrophy. After 4 weeks, using the rota-rod and treadmill tests in the same methods as in Examples 4-2 and 4-3, the motor ability was confirmed (FIG. 15).

As a result, it was confirmed that the motor ability was improved in the group that was fed with cetylpyridinium chloride, compared to the control group.

From the foregoing, those skilled in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

What is claimed is:

1. A method for treating a disease associated with muscle weakness comprising administering a compound selected from the group consisting of butylpyridinium, dodecylpyridinium, cetylpyridinium or a pharmaceutically acceptable salt thereof, to a subject in need of treating the disease, wherein the disease is selected from the group consisting of sarcopenia, muscular atrophy, muscular dystrophy, and acardiotrophy.

2. The method of claim 1, wherein the muscular dystrophy is Duchenne muscular dystrophy or Becker muscular dystrophy.

3. The method of claim 1, wherein the salt is selected from the group consisting of butylpyridinium chloride, dodecylpyridinium chloride, cetylpyridinium chloride, butylpyridinium bromide, dodecylpyridinium bromide, and cetylpyridinium bromide.

4. The method of claim 1, wherein the concentration of the butylpyridinium, dodecylpyridinium, cetylpyridinium, or a pharmaceutically acceptable salt thereof is in the range from 0.001 μM to 5.0 μM.

* * * * *